(12) United States Patent
Qvist

(10) Patent No.: US 6,335,430 B1
(45) Date of Patent: Jan. 1, 2002

US006335430B1

(54) PROCESS OF PRODUCING POLYPHENOLIC ADHESIVE PROTEINS AND PROTEINS PRODUCED IN ACCORDANCE WITH THE PROCESS

(76) Inventor: Magnus Qvist, Hästhagvaägen 6, Floda (SE)

( * ) Notice: Subject to any disclaimer, the term of this patent is extended or adjusted under 35 U.S.C. 154(b) by 0 days.

(21) Appl. No.: 09/722,417

(22) Filed: Nov. 28, 2000

Related U.S. Application Data

(63) Continuation of application No. 09/407,092, filed on Sep. 28, 1999, now abandoned.

(30) Foreign Application Priority Data

Sep. 28, 1998 (SE) ................................................ 9803274

(51) Int. Cl.[7] ............................ C07K 1/14; C07K 1/30; C07K 14/435
(52) U.S. Cl. ...................... 530/419; 530/420; 530/423; 530/425; 530/857
(58) Field of Search ........................... 100/124.3, 124.4, 100/124.7; 514/12.21; 530/350, 419, 420, 422, 423, 425, 855, 857

(56) References Cited

U.S. PATENT DOCUMENTS

| 4,496,397 A | 1/1985 | Waite | 106/161 |
|---|---|---|---|
| 4,585,585 A | 4/1986 | Waite | 530/328 |

OTHER PUBLICATIONS

J. Pardo et al., "Purification of Adhesive Proteins from Mussels", pp. 147–150, Protein Expression and Purification, vol. 1, 1990.

*Primary Examiner*—Jeffrey E. Russel
(74) *Attorney, Agent, or Firm*—Young & Thompson

(57) ABSTRACT

The invention relates to a process of producing MAP-products from mussel feet. The process is characterised by extracting the mussel feet in a weakly acid aqueous solution containing, for instance, 1–10 percent by weight of a weak acid and 0.5–3 percent by weight of perchloric acid, whereafter the proteins in the aqueous solution are precipitated by adding inorganic or organic salts and separated from the system, subsequent to having extracted the solid substances.

6 Claims, No Drawings

PROCESS OF PRODUCING POLYPHENOLIC ADHESIVE PROTEINS AND PROTEINS PRODUCED IN ACCORDANCE WITH THE PROCESS

CROSS-REFERENCE TO RELATED APPLICATIONS

This application is a continuation of application Ser. No. 09/407,092, filed Sep. 28, 1999, now abandoned.

FIELD OF INVENTION

The present invention relates to a process of producing polyphenolic adhesive proteins from mussel feet, such proteins being referred to here as MAP. The invention also relates to MAP-products produced by the process.

BACKGROUND OF THE INVENTION

The term MAP is an acronym of the English term Mussel Adhesive Protein. The designation is based on the production of the protein concerned from a gland in the feet of mussels. The protein adheres strongly to all types of surfaces, e.g. to live cells and to other materials such as stone, wood and similar materials located under water. The mussels thus adhere to some appropriate underwater object and there live out their lives.

Mussel adhesive protein has a molecular weight of about 130,000 and consists of 75–85 repeated sequences of hexapeptides and decapeptides. The protein contains up to 20% lysine and an unusually high proportion, up to 50%, of hydroxy-containing amino acids, such as hydroxy prolines, serines, treonines, tyrosines, and (what is highly unusual in a polypeptide) 3,4-dihydroxyphenylalanine (DOPA). The DOPA groups constitute 10–15% of the adhesive protein.

The adhesive strength of MAP per unit of weight is comparable with that of synthetic cyanoacrylate and epoxy resins. MAP is also water-resistant and binds very effectively in water and adheres very effectively to many solid and semi-solid surfaces, such as to glass, metal, biological tissue and plastics, even to Teflon® surfaces.

The high lysine concentration of mussel adhesive protein probably contributes to its good adhesion, particularly via ion bonds to negatively charged surfaces, such as to many proteins and polysaccharides.

The very high hydroxyl content and the orthodiphenolic nature of the DOPA groups are probably responsible for the unique water-repellent property of mussel adhesive protein and, consequently, for its ability to adhere to under water objects and to cure in such environments.

The hydroxyamino acids also contribute significantly towards hydrogen bonds in achieving the adhesive strength.

The orthodiphenolic DOPA-radicals form strong chelates with metal ions and oxides and semimetals such as silicon. This is an essential part of the ability of mussel adhesive protein to adhere to stone, glass and like surfaces.

DOPA is oxidised to a quinone through molecular oxygen and is considered to react with biogenic amines to form strong covalent bonds. Intermolecular bonds to, inter alia, lysine radicals are contributory to the "inner" adhesion and a stronger adhesive bond.

Mussel adhesive protein is well tolerated in biological systems. It is non-toxic and is generally biocompatible and exhibits but small or no antigenicity. This makes it potentially useful for many purposes, such as with adhesive biofilm for immobilising cells and enzymes, as a moisture compatible adhesive for dental treatment, as an additive to or a replacement for sutures in the treatment of wounds and sores, for fixating and healing complicated bone fractures, as a matrix for medicines that have a delayed effect, and so on. Mussel adhesive protein can also be used as an anti-corrosive agent simply by coating, e.g., steel surface with a thin mussel adhesive protein film that binds to the iron atoms in the steel.

A process for producing mussel adhesive protein that contains DOPA and hydroxy proline (hyp) is described in U.S. Pat. No. 4,496,397. This process is based on mussel feet and involves forming an aqueous extract of the proteins to which there is then added a borate at pH 7.0–9.0 to produce a soluble borate complex of the DOPA-containing protein whilst precipitating out the impurities. The borate complex is then separated and treated in various ways, such as with an acetic acid solution or lyophilized in an inert atmosphere. The proteins produced in accordance with this process have a purity factor of at least 0.10, whereas a product of maximum purity should have a factor greater than 0.16.

A further process of producing mussel adhesive protein is described in the publication Protein Expression and Purification 1 147 150 (1990). This publication describes the production of mussel adhesive protein (MAP) on the basis of mussel feet, where the proteins are extracted in a solution containing Tris-HCL (pH 7.5, the pH buffer) NaCl, EDTA (Ethylenediaminetetraacetic acid), EGTA (Ethylene glycol bis(amino allyl ether) N,N,N,N, tetra acetic acid), PMSF (Phenylmethylsulphonylfluoride), KCN, NEM (N-Ethyl maleamide) and trypsine-inhibitor from soya beans. The suspension is separated into a solid and a liquid layer and the solid layer is homogenized in diluted acetic acid that contains PMSF and 2-mercaptoethanol. Subsequent to centrifugation, concentrated perchloric acid is added dropwise to the liquid layer which is then centrifuged and the liquid layer again collected. The liquid layer is then mixed with cold acetone that contains TritonX 100, HCL and 2-mercaptoethanol. The mussel adhesive proteins then precipitate and are recovered for later processing.

Technical Problem

The aforedescribed process and also other known process for the production of mussel adhesive proteins require the use of a number of auxiliary chemicals and result in a low yield and relatively impure products in respect of certain mussel species. They are also time-consuming and uneconomical.

Solution

It has long been desired to produce mussel adhesive proteins in an economic manner on a larger scale while obtaining products of desired purity. Accordingly, there is provided in accordance with the present invention a process of producing mussel adhesive protein products from mussel feet. The process is characterised by extracting the mussel feet in a weakly acid aqueous solution that contains, e.g., 1–10 percent by weight of a weak acid and 0.5–3 percent by weight perchloric acid, whereafter solid substances are removed from the solution and the proteins precipitated by adding organic or inorganic salts and the protein precipitate then separated from the solution.

According to the invention, convenient precipitation salts are sodium chloride, potassium chloride, ammonium sulphate, ammonium acetate, sodium sulphate, potassium sulphate in a concentration of 5–15 percent by weight of the solution.

According to the invention, the separated proteins are suitably re-dissolved in diluted acetic acid and the non-dissolved material is then separated from the system.

According to the invention, perchloric acid is suitably added to the re-dissolved and separated protein solution for selective precipitation of undesirable proteins, whereafter the precipitate is separated from the system.

According to the invention, it is beneficial to subject the separated solution to dialysis in diluted acetic solution, in order to remove perchloric acid and low molecular weight material. According to the invention, the mussel adhesive protein in solution can be precipitated out by adding ethanol, propanol or acetone, and then separated from the system and optionally re-dissolved in diluted acetic acid.

The invention also relates to mussel adhesive proteins produced in accordance with the above process.

DETAILED DESCRIPTION OF THE INVENTION

The inventive process is performed on mussel feet, which may be deep-frozen, which are added to an aqueous mixture that contains acetic acid in a concentration of 1–10%, preferably in the region of 5%, and perchloric acid in a concentration of 0.5–3%, preferably in the region of 1.5%. The extraction mixture is then homogenised in a mixer for some minutes, whereafter the suspension is centrifuged at high speed, e.g. a speed that generates 15,000 G for instance.

The aqueous solution containing the mussel adhesive proteins is collected and the MAP-proteins precipitated by adding inorganic salts, preferably sodium chloride, in high concentration. It is necessary for the concentration of these organic salts to be high, in the region of 10 percent by weight. At this high salt concentration, the mussel adhesive proteins will precipitate out while the major part of other, non-interesting proteins remain in solution. The mussel adhesive proteins will also dissolve out at lower concentrations. The precipitating chemical is not restricted to just sodium chloride. Potassium chloride, ammonium sulphate, sodium sulphate, etc., may alternatively be used to this end. After a couple of hours in a refrigerator, there will have formed a precipitate which is then removed from the system, suitably by centrifugation at 5,000 G for instance.

This MAP-precipitate may be used directly without further purification in some instances. In such cases it may optionally be mixed with other substances, e.g. collagen, as a reinforcement and used on wounds or the like, wherewith water is applied and the MAP-protein will bind both to itself and to the surroundings.

However, the MAP-precipitate may alternatively be dissolved in 5%-acetic acid for instance, wherewith certain undesired proteins will be precipitated. The mixture may then be centrifuged so as to separate undissolved material therefrom, which is then removed from the system.

The MAP-mixture can be further purified by adding perchloric acid thereto, wherewith undesirable dissolved material will precipitate. The perchloric acid, being of a concentration in the region of 15%, is preferably added slowly to the mixture and in an amount corresponding to 5–15% of the volume of the solution. The mixture is then cooled for half an hour and the precipitate removed, suitably by centrifugation.

A highly pure mussel adhesive protein product can be obtained, by then dialysing the solution, preferably from two to three times, in large volumes in weak acetic acid, for instance 3%-acetic acid, wherewith undesirable perchloric acid migrates out through the dialysis membrane together with material of low molecular weight. These dialysis process are generally known and need not therefore be described in detail here. The dialysis results in a MAP-product having a purity of 90–97% and a yield of 1–2 mg mussel adhesive protein per gram of mussel foot starting material.

The aqueous MAP-solution treated with perchloric acid may also be purified by precipitating the mussel adhesive protein with the aid of acetone in an acid environment, suitably overnight. The precipitate is separated, preferably by centrifugation, and is then dissolved in a small volume of 5%-acetic acid. The protein will then have a purity of 95–100%, while the yield drops slightly in relation to the yield obtained by dialysis, namely to 0.5–1 mg mussel adhesive protein per gram of mussel foot starting material.

Extreme purity can be obtained by combining the two purification processes using dialysis and acetone precipitation.

The invention thus provides a process of producing mussel adhesive proteins that have varying degrees of purity and that are adapted for different usages, in a particularly simple manner without the use of a large number of unnecessary chemicals and in a simple and economic manner.

The invention is not restricted to the aforedescribed embodiment and variations can be made within the scope of the accompanying Claims.

What is claimed is:

1. A process of producing polyphenolic adhesive proteins from mussel feet, characterised by extracting the mussel feet in a weakly acid aqueous solution containing 1–10 percent by weight of a weak acid and 0.5–3 percent by weight of perchloric acid, separating solid substances from the proteins in said aqueous solution, precipitating the proteins in said aqueous solution after removal of solids by adding a salt thereto, and separating said proteins.

2. A process according to claim 1, characterised in that the salt is at least one member selected from the group consisting of sodium chloride, potassium chloride, ammonium sulphate, ammonium acetate, sodium sulphate and potassium sulphate in a concentration of 5–15 percent by weight of said solution.

3. A process according to claim 1, characterised by redissolving the separated proteins in diluted acetic acid and thereafter removing undissolved material from the redissolved proteins.

4. A process according to claim 3, characterised by adding perchloric acid to the re-dissolved proteins so as to selectively precipitate undesired proteins, and then separating the precipitate from unprecipitated proteins.

5. A process according to claim 4, characterised by subjecting the unprecipitated proteins to dialysis in a diluted acetic acid solution so as to remove perchloric acid and low molecular weight material from the unprecipitated proteins.

6. A process according to claim 4, characterised by adding ethanol, propanol or acetone to the solution from which the undesired protein precipitate has been separated to precipitate the polyphenolic proteins therefrom, separating said polyphenolic proteins and optionally redissolving said separated polyphenolic proteins in diluted acetic acid.

* * * * *